(12) United States Patent
Darmenton et al.

(10) Patent No.: US 6,241,785 B1
(45) Date of Patent: Jun. 5, 2001

(54) USE OF FLAVYLIUM TYPE COMPOUNDS NON-SUBSTITUTED IN POSITION 3 FOR DYEING KERATINOUS FIBRES AND COMPOSITIONS CONTAINING THEM

(75) Inventors: Patrick Darmenton, Bourg la Reine; Michel Philippe, Wissous, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/331,443

(22) PCT Filed: Dec. 3, 1997

(86) PCT No.: PCT/FR97/02196

§ 371 Date: Aug. 20, 1999

§ 102(e) Date: Aug. 20, 1999

(87) PCT Pub. No.: WO98/27940

PCT Pub. Date: Jul. 2, 1998

(30) Foreign Application Priority Data

Dec. 23, 1996 (FR) .................................................. 96 15890

(51) Int. Cl.$^7$ ...................................................... A61K 7/13
(52) U.S. Cl. .......................... 8/426; 8/405; 8/424; 8/579; 8/657; 8/659
(58) Field of Search ............................. 8/405, 424, 426, 8/579, 657, 659

(56) References Cited

U.S. PATENT DOCUMENTS

| | | | |
|---|---|---|---|
| 3,266,903 | 8/1966 | Jurd | 99/103 |
| 3,597,151 | * 8/1971 | Baumann et al. | 8/657 |
| 4,208,434 | 6/1980 | Iacobucci et al. | 426/72 |
| 4,376,781 | * 3/1983 | Lietti et al. | 424/283 |

FOREIGN PATENT DOCUMENTS

| | | |
|---|---|---|
| 0 024 731 | 3/1981 | (EP) . |
| 2 009 159 | 6/1979 | (GB) . |
| WO 94/06787 | 3/1994 | (WO) . |
| WO 96/37558 | 11/1996 | (WO) . |

OTHER PUBLICATIONS

Rey et al, Isolation and Composition of a Natural Dye from the Stems of *Sorghum bicolor* (*L*.) Moench Subsp. amer. caudatum, Cereal Chem, Abstract, 1993 (no month available).*

M. Kouda–Bonafos et al., "Isolation of Apigeninidin From Leaf Sheats of Sorghum caudatum", Journal of Chemical Ecology, vol. 20, No. 8, Aug. 1994, pp. 2123–2125.

D. Pratt et al., "A Synthesis of Pyrylium Salts of Anthocyanidin Type", Journal of the Chemical Society, 1923, pp. 745–759.

A. Robertson et al., "A Synthesis of Pyrylium Salts of Anthocyanidin Type. Part IX. Some Hydroxyflavylium Salts", Journal of The Chemical Society, Jul. 1926, pp. 1951–1959.

A. Robertson et al., "A Synthesis of Pyrylium Salts of Anthocyanidin Type", Journal of The Chemical Society, 1927, pp. 2196–2207.

A. Robertson et al., "A Synthesis of Pyrylium Salts of Anthocyanidin Type. Part XV. The Synthesis of Cyanidin Chloride by Means of O–Benzoylpholoroglucinaldehyde", Journal of The Chemical Society, Jan. 1928, pp. 1526–1537.

J.G. Sweeny et al., "Synthesis of Anthocyanidins—The Oxidative Generation of Flavylium Cations Using Benzoquinones", Tetrahedron, vol. 33, 1977, pp. 2923–2926.

J.G. Sweeny et al., "Synthesis of Anthocyanidins—The Synthesis of 3–deoxyanthocyanidins From 5–hydroxy–flavanones", Tetrahedron, vol. 33, pp. 2927–2932, 1977.

J. Bell et al., Experiment son the Synthesis of Anthocyanins. Part XX. Synthesis of Malvidin 3–Galactoside and its Probable Occurrence as a Natural Anthocyanin, Journal of The Chemical Society, 1934, pp. 813–818.

* cited by examiner

*Primary Examiner*—Caroline D. Liott
(74) *Attorney, Agent, or Firm*—Finnegan Henderson Farabow Garrett & Dunner, L.L.P.

(57) ABSTRACT

The invention concerns the use of flavylium type compounds, non-substituted in position 3, and substituted by at least a hydroxyl or alcoxy radical, in particular Apigenidin, in pure form or in the form of plant extracts containing them, as coloring agent in or for making compositions for dyeing keratinous fibers, particularly human keratinous fibers such as hair. The invention also concerns the dyeing compositions containing them, particularly cosmetic compositions for direct hair dyeing, and the corresponding dyeing method. The hair dyes resulting from the use of these coloring agents are particularly stable to light and washing.

33 Claims, No Drawings

USE OF FLAVYLIUM TYPE COMPOUNDS NON-SUBSTITUTED IN POSITION 3 FOR DYEING KERATINOUS FIBRES AND COMPOSITIONS CONTAINING THEM

The invention relates to the use of flavylium-type compounds non-substituted in position 3, and substituted by at least one hydroxyl or alkoxy radical, and in particular Apigenidin, as colouring agents, in or for the manufacture of compositions for dyeing keratinous fibres, in particular human keratinous fibres such as hair.

Many compounds containing a flavylium ring (F):

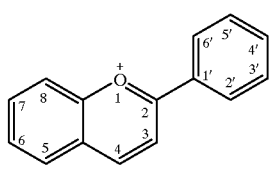

(F)

constitute the basic structure of natural colouring agents which are responsible for most of the red, blue or purple colours of flowers or fruits worldwide, and which are commonly known as "anthocyanins" or alternatively "anthocyanidins", in the case of the aglycone form of anthocyanins.

The majority of anthocyanins and anthocyanidins contain, respectively, a glycoside or hydroxyl radical in position 3 of the flavylium ring.

These anthocyanins and anthocyanidins were previously widely used as natural colouring agents for dyeing textiles. Their use for this application was then abandoned because of the lack of fastness of the colours obtained to light and to washing.

It is well known, see in this respect patent U.S. Pat. No. 3,266,903, that the instability to light of these natural colouring agents is dependent on the nature of the substituent in position 3 of the flavylium ring. When position 3 of the flavylium ring is occupied by a sugar, as is the case for anthocyanins, or by a hydroxyl radical, as is the case for their aglycone form, the anthocyanidins, the colours are unstable. Thus, in the food industry, it has been recommended to prevent the decolorization, caused by light, of compositions containing these anthocyanin and anthocyanidin colouring agents which are not very stable, by photo-stabilizing them by combining with flavonols (EP-24 731 A1), or with ascorbic acid derivatives (U.S. Pat. No. 4,208,434).

Moreover, in the field of hair dyeing, direct dyes are being sought which, without supplying an oxidizing agent, are capable of modifying by themselves the natural shade of hair, temporarily.

In this application, the colouring agents must satisfy a number of criteria: be as harmless as possible, that is to say exhibit acceptable innocuousness and generate reproducible colours which are sufficiently resistant, in particular, to light, washing and adverse weather conditions.

In addition, these colouring agents, as is well known, are used in the form of mixtures, in order to obtain natural shades.

However, in this field, the so-called natural colouring agents such as Henna generate only a range of shades close to blond. To broaden the pallet of colours, it is necessary to find other natural colouring agents whose shades are similar to the basic colours and which, when mixed in particular with Henna, can meet the expectations of consumers.

It is after major research studies carried out on this subject that the Applicant has now discovered, completely unexpectedly and surprisingly, flavylium-type compounds non-substituted in position 3 and substituted by at least one hydroxyl or alkoxy radical, which make it possible to dye intensely, and without oxidizing agent, keratinous fibres, and in particular human keratinous fibres such as hair, in shades which are particularly stable to light and to shampooing.

It has been observed, in addition, that the hair dyes resulting from the use of these compounds preserved the condition of the hair, were reproducible and exhibited excellent innocuousness.

This discovery forms the basis of the present invention.

The subject of the present invention is thus the use of flavylium-type compounds non-substituted in position 3, and substituted by at least one hydroxyl or alkoxy radical, in pure form or in the form of plant extracts containing them, as colouring agents, in or for the preparation of a composition for dyeing keratinous fibres, in particular cosmetic compositions for the direct dyeing of human keratinous fibres such as hair.

Among these flavylium-type compounds, there are preferably used the compounds substituted in position 4' by a hydroxyl, alkoxy or hydroxyalkyl radical, in pure form or in the form of plant extracts containing them.

There are still more particularly used the flavylium-type compounds as described above and of the following formula (I):

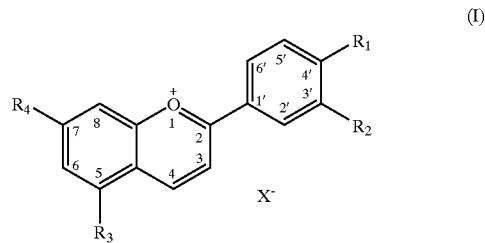

(I)

in which formula (I):
  $R_1$ denotes an OH radical or a saturated or unsaturated, linear or branched $C_1$–$C_8$ alkoxy radical,
  $R_2$, $R_3$ and $R_4$, which are identical or different, denote H or $R_1$, it being understood that at least one of the radicals $R_1$ to $R_4$ denotes OH,
  X is an anion preferably denoting a halogen or a radical:

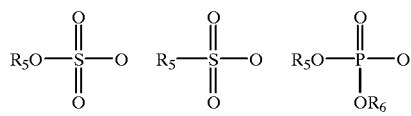

in which $R_5$ and $R_6$ are saturated or unsaturated, linear or branched $C_1$–$C_8$ alkyl radicals, in pure form or in the form of plant extracts containing them.

Another subject of the invention is a composition for dyeing keratinous fibres, in particular a cosmetic composition for the direct dyeing of human keratinous fibres such as hair, comprising, in a medium appropriate for dyeing, at least one flavylium-type compound non-substituted in position 3 and substituted by at least one hydroxy or alkoxy radical, and such as those defined above, in a pure form or in the form of a plant extract containing it.

Its subject is also the methods of dyeing using these compositions.

However, other characteristics, features and advantages of the invention will appear even more clearly on reading the description which follows, as well as the various concrete, but not at all limiting, examples intended to illustrate it.

For the purposes of the invention, keratinous fibres are mainly understood to mean natural textile fibres such as wool, human keratinous fibres such as in particular hair, body hair, eyelashes and eyebrows. The invention relates more particularly to hair.

The compounds of formula (I) which are particularly preferred according to the present invention are chosen from the group of those for which, in formula (I), $R_1$ denotes OH or $OCH_3$.

There may be mentioned in particular among them the chlorides of the following compounds:

4',5,7-trihydroxyflavylium, commonly called "Apigenidin chloride",

3',4',7-trihydroxyflavylium,

4'-hydroxyflavylium,

4',7-dihydroxyflavylium,

3',4'-dihydroxyflavylium,

3',4'-dihydroxy-7-methoxyflavylium.

Among these compounds, Apigenidin chloride (4',5,7-trihydroxyflavylium) and 3',4',7-trihydroxyflavylium chloride are even more particularly preferred.

A specific form of the invention consists in using Apigenidin chloride in the form of a plant extract which can easily be prepared by extraction and isolated from *Sorghum caudatum* leaves, as has, for example, been described and prepared by the authors Kouda-Bonafos, Czyzewska, Nacro and Oehlschlager in Journal of Chemical Ecology-1994-Vol. 20, No. 8-pages 2123–2125.

It can also be extracted from the stems, seeds or leaves of *Sorghum bicolore*, from the petals of *Gesneria fulgens*, as well as from the species *Blechum, Procerum* and *Sorgho* contaminated by *Colletotrichum graminicola*.

A plant extract of *Sorghum caudatum* having a titre approximately greater than 70% by weight of apigenidin chloride is particularly preferred according to the present invention.

The flavylium-type compounds non-substituted in position 3 and substituted by at least one hydroxyl or alkoxy radical according to the invention can be easily obtained by the synthesis route, and at a low cost, especially by the well-known method of R. Robinson and D. D. Pratt [(J., Chem. Soc., 745 (1923)]. The said method involves condensing an ortho-hydroxybenzaldehyde or its substitution derivatives with acetophenone or its substitution derivatives in order to obtain, by choosing the substituents, the desired compounds of formula (I).

By taking as an example Apigenidin chloride (4',5,7-trihydroxyflavylium chloride), the synthesis scheme (i) may be the following:

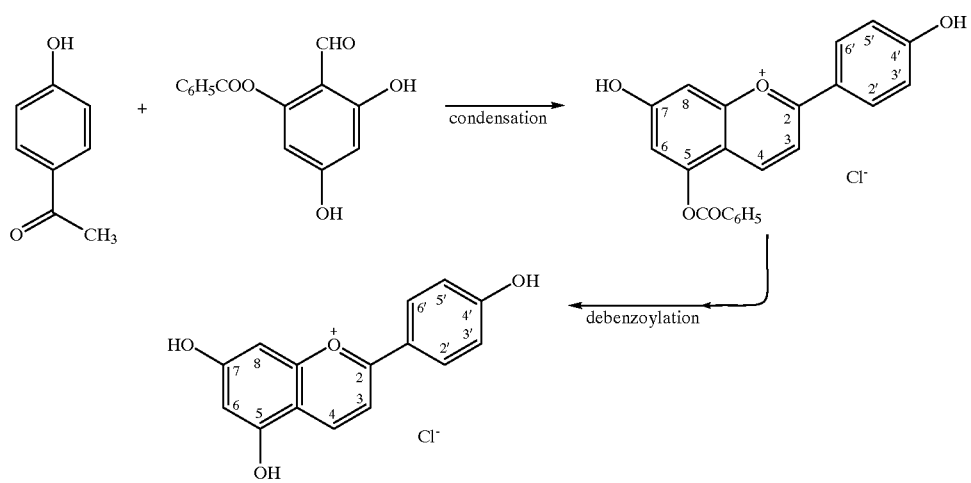

By taking as an example 3',4',7-trihydroxyflavylium chloride, the synthesis scheme (ii) may be the following:

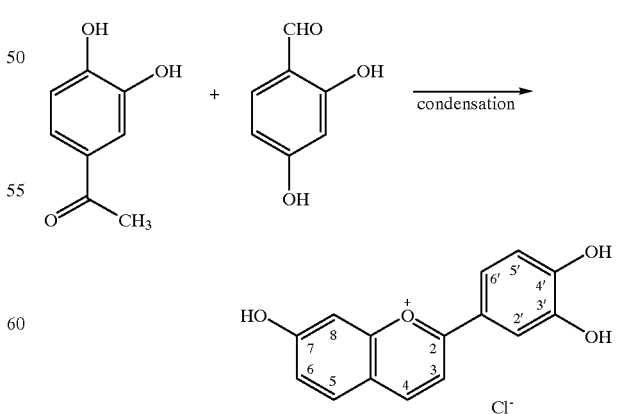

Various synthesis routes, well-known in the prior art, lead to Apigenidin.

One method consists, for example, in preparing, in a first step, trimethylapigenidin by condensation of commercially available 4,6-dimethoxy-2-hydroxybenzaldehyde with commercially available 4-methoxyacetophenone at 0° C. in anhydrous ether medium, and saturation with anhydrous HCl in order to obtain, after filtration, an orange-red precipitate of trimethylapigenidin. In a second step, in hydrolysing the trimethylapigenidin obtained in the preceding step to apigenidin chloride, the reaction being carried out in an HI and phenol and AgCl medium in solution in methanol. Such a method of synthesis is described by R. Robinson and A. Robertson in J., Chem., Soc. 1951-(1926) and 2196-(1927).

Another method consists in condensing 2,4,6-trihydroxybenzaldehyde with 4-hydroxyacetophenone at 0° C. in anhydrous solvent medium (ethyl acetate for example), and saturating with anhydrous HCl, in order to obtain apigenidin chloride. Such a method is described by R. Robinson and A. Robertson in J., Chem., Soc. 1528-(1928).

Another method of preparing apigenidin chloride consists in reducing a flavone, Naringenin, or its triacetylated derivative, with $BH_4Na$, and then in oxidizing the product obtained with chloranil (tetrachloro-1,4-benzoquinone). The said method is described by J. G. Sweeny and G. A. Iacobucci in the journal Tetrahedron 33–2923 and 2927-(1977).

The method most particularly preferred, according to the present invention, consists in condensing 2,4-dihydroxy-6-benzoylbenzaldehyde with 4-hydroxyacetophenone at 0° C. in anhydrous ethyl acetate medium, in saturating with anhydrous HCl, and then in debenzoylating the product obtained with sodium hydroxide in order to obtain apigenidin chloride with a high yield, according to the scheme (i) described above.

The said method is described by R. Robinson and J. C. Bell in J., Chem., Soc. 813-(1934).

The concentration of flavylium-type compound, as described according to the present invention, is preferably between about 0.05 and 20%, and still more preferably between 0.1 and 10% by weight relative to the total weight of the dyeing composition.

The dyeing composition according to the invention may optionally contain, in order to vary the shades or alternatively to enrich their shimmer, in addition to the flavylium-type compounds non-substituted in position 3 of the invention, another (other) natural direct dye(s) well known in the state of the art, and in particular 2,3-indolinedione commonly called isatin, hydroxyanthraquinones or benzoquinones, or another (other) synthetic direct dye(s) conventionally used in direct hair dyeing, such as for example nitrobenzene dyes, nitropyridines, anthraquinone dyes, mono- or diazo, triarylmethane, azine, acridine and xanthene dyes, or alternatively metalliferous dyes.

The proportion of all these other direct dyes for addition may vary between about 0.05 and 10% by weight relative to the total weight of the dyeing composition.

The appropriate medium for dyeing is preferably an aqueous medium consisting of water and/or cosmetically acceptable organic solvents, and more particularly alcohols such as ethyl alcohol, isopropyl alcohol, benzyl alcohol and phenylethyl alcohol, or glycols or glycol ethers such as, for example, ethylene glycol and its monomethyl, monoethyl and monobutyl ethers, propylene glycol or its ethers such as, for example, propylene glycol monomethyl ether, butylene glycol, dipropylene glycol as well as diethylene glycol alkyl ethers such as, for example, diethylene glycol monoethyl ether or monobutyl ether, in concentrations of between about 0.5 and 20% and, preferably, between about 2 and 10% by weight relative to the total weight of the composition.

It is also possible to add to the composition according to the invention fatty amides such as mono- and diethanolamides of acids derived from copra, lauric acid or oleic acid, at concentrations of between about 0.05 and 10% by weight.

It is also possible to add to the composition according to the invention surfactants well known in the state of the art and of the anionic, cationic, non-ionic, amphoteric or zwitterionic type or mixtures thereof, preferably in a proportion of between about 0.1 and 50% by weight and advantageously between about 1 and 20% by weight relative to the total weight of the composition.

It is also possible to use thickening agents in a proportion ranging from about 0.2 to 5%.

The said dyeing composition may contain, in addition, various customary adjuvants such as antioxidants, perfumes, sequestering agents, dispersing agents, hair conditioning agents, preservatives, opacifying agents, as well as any other adjuvant normally used in dyeing keratinous fibres.

Of course, persons skilled in the art will be careful to choose the possible additional compounds mentioned above, such that the advantageous properties intrinsically attached to the dyeing composition according to the invention are not, or not substantially, altered by the addition(s) envisaged.

The dyeing composition according to the invention may be formulated at acidic, neutral or alkaline pH, it being possible for the pH to vary for example from 2 to 11 and preferably from 5 to 10, and it being possible for it to be adjusted by means of alkalinizing agents or acidifying agents or buffers well known in the prior art.

As alkalinizing agents, there may be mentioned ammonium hydroxide, alkali metal carbonates, alkanolamines, for example mono-, di- and triethanolamines and derivatives thereof, sodium or potassium hydroxides, and the compounds of formula:

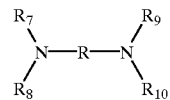

in which R is a propylene residue optionally substituted with a hydroxyl group or a $C_1$–$C_4$ alkyl radical; $R_7$, $R_8$, $R_9$ and $R_{10}$, simultaneously or independently of each other, represent a hydrogen atom, a $C_1$–$C_4$ alkyl or $C_1$–$C_4$ hydroxyalkyl radical.

The acidifying agents are conventionally inorganic or organic acids such as for example hydrochloric, tartaric, citric and phosphoric acids. Among the buffers, there may be mentioned for example potassium dihydrogen phosphate/sodium hydroxide.

The composition according to the invention, for dyeing keratinous fibres, may be provided in various forms, such as in the form of a liquid, cream, gel, cataplasm or in any other form appropriate for dyeing keratinous fibres. In particular, it may be packaged under pressure in an aerosol can in the presence of a propellent and can form a foam.

Another subject of the present invention relates to a method of dyeing human keratinous fibres, in particular hair, by direct dyeing, consisting in allowing a dyeing composition containing at least one flavylium-type compound non-substituted in position 3, and substituted by at least one hydroxyl or alkoxy radical, to act on the dry or wet fibres.

It is possible to use the composition according to the invention as a leave-in composition, that is to say that after application of the composition to the fibres, they are dried without intermediate rinsing. In the other modes of application, the composition is allowed to act on the fibres for an exposure time varying between about 3 and 60 minutes, preferably between about 5 and 45 minutes, at a temperature varying between about 20° C. and 50° C., they are rinsed, optionally washed, then rinsed again, and dried.

Concrete examples illustrating the invention will now be given.

PREPARATION EXAMPLE

EXAMPLE 1

Preparation of 4',5,7-Trihydroxyflavylium Chloride or Apigenidin Chloride

First step:
Synthesis of 2-benzoylphloroglucinaldehyde

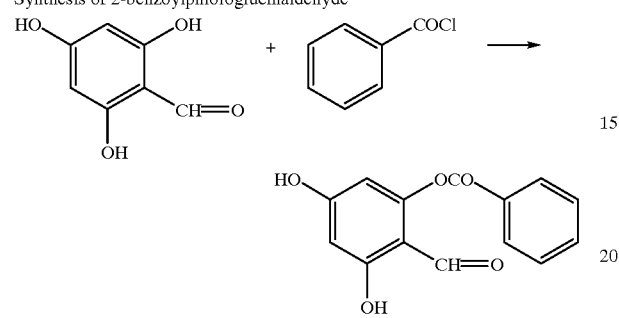

250 ml of water and 15.4 g (0.1 mol) of 2,4,6-trihydroxybenzaldehyde were placed in a one-liter three-necked round-bottomed flask. The mixture was cooled to 7° C. and 5.6 g (0.1 mol) of KOH in 50 ml of water were added. The mixture was vigorously stirred for 30 minutes and then cooled to −5° C.

At the maximum stirring, 14 g (11 ml) of freshly distilled benzoyl chloride were added to the solution in three portions. The mixture was thus stirred until the benzoyl chloride odour disappeared and then an excess of bicarbonate was slowly poured into the solution. The orange-coloured precipitate of 2-benzoylphloroglucinaldehyde obtained was drained on sintered glass and then was rinsed with bicarbonate, then with water and finally dried in a desiccator.

Step two:
Synthesis of benzoylapigenidin

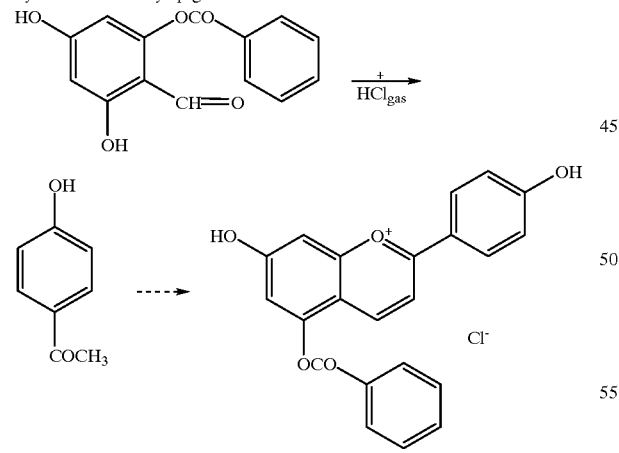

25.8 g (0.1 mol) of 2-benzoylphloroglucinaldehyde obtained in the preceding step were placed with 50 g (0.37 mol) of 4-hydroxyacetophenone in a 500-ml two-necked round-bottomed flask containing 300 ml of anhydrous ethyl acetate (freshly distilled) The solution was saturated, at 0° C., with anhydrous gaseous HCl by bubbling for 35 minutes, and the stirring was continued at 0° C. for 78 hours. A dark red which was drained and which was benzoylapigenidin—yield: 75%.

Third step:
Synthesis of apigenidin chloride

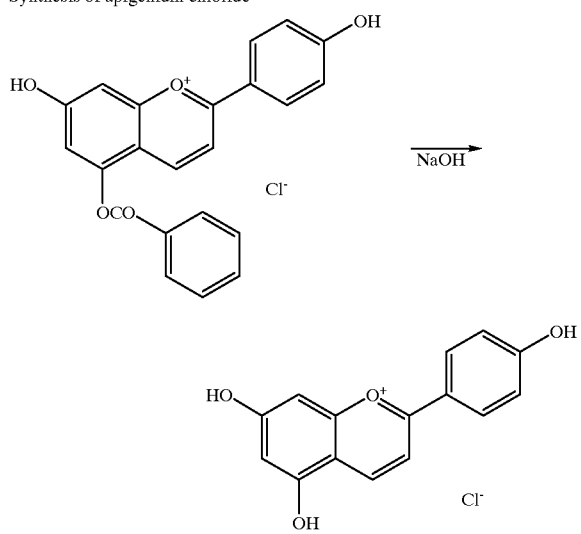

The product obtained in the preceding step was debenzoylated by stirring it in a 10% sodium hydroxide solution, at room temperature, for 5 hours. The solution was acidified with concentrated HCl, heated on a water bath for 10 minutes and then the product recrystallized. Apigenidin chloride was obtained with a 60% yield.

EXAMPLE 2

Preparation of 3',4',7-trihydroxyflavylium

First step:
Synthesis of 3, 4-dihydroxyacetophenone

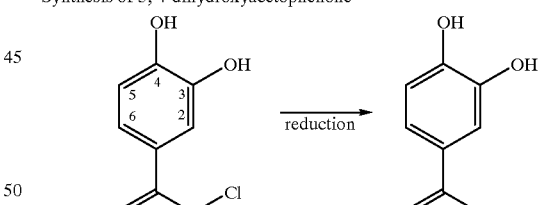

20 g of 2'-chloro-3,4-dihydroxyacetophenone were added to 20 g of zinc (previously pickled with 2 N hydrochloric acid, then washed with water to neutrality and then kept in an oven), in 600 ml of a 4/1 mixture of tetrahydrofuran and glacial acetic acid. The mixture was stirred at room temperature for 3 days. It was then filtered and the tetrahydrofuran evaporated off. The residue was dissolved in ethyl acetate and then washed with water and dried over magnesium sulphate. The ethyl acetate was then evaporated off. Next the product obtained was crystallized from a 1/1 ethyl acetate/hexane mixture, and finally 80% of a white solid was obtained by recrystallization from ethanol or from methanol.

Second step:
Synthesis of 3', 4', 7-trihydroxyflavylium chloride.

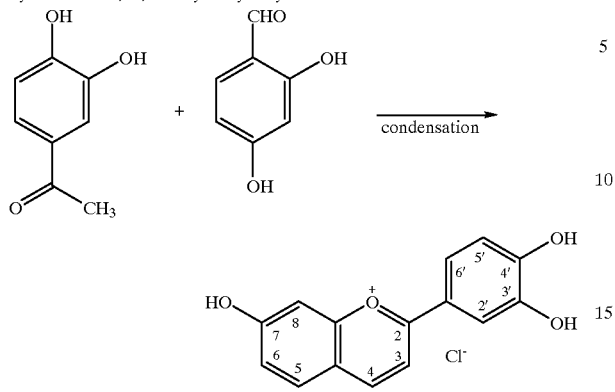

At 0° C., hydrochloric acid (generated by dropwise addition of $H_2SO_4$ to NaCl) was bubbled in a two-necked flask containing 12 g (0.079 mol) of 3,4-dihydroxyacetophenone, 10.88 g (0.079 mol) of 2,4-dihydroxybenzaldehyde and 100 ml of ethyl acetate distilled beforehand. The product started to precipitate after 30 minutes. The bubbling was continued for another 1 hour and then the reaction was stopped. The solution was kept at −18° C. for 3 days and then it was filtered. The filtrate was evaporated and it was taken up in ether; the product precipitated. It was separated from the ether, dissolved in hot methanol and then it was added slowly to an equivalent volume of acetone. The solution was placed in a refrigerator and the product started to precipitate. After filtration, the filtrate was evaporated, dissolved in a minimum of methanol and then ether was added until a precipitate appeared. The procedure was thus repeated several times until precipitate no longer appeared. The purity of the 3',4',7-trihydroxyflavylium chloride precipitate thus obtained with a yield of 75% was checked by HPLC (high-performance liquid chromatography).

EXAMPLES OF APPLICATION

EXAMPLE 3

The following dyeing composition was prepared:
3',4',7-Trihydroxyflavylium chloride
prepared in Example 2 0.29 g
Hydroxyethylcellulose 2.30 g
Citric acid 1.40 g
Aqueous solution of NaOH qs pH 2.65
Demineralized water qs 100 g The above composition was applied to locks of natural grey hair and also to locks of permanently-waved grey hair, which was 90% white, at the rate of 2 grams of composition per gram of hair. It was allowed to act for 30 minutes at room temperature. After rinsing with running water and drying, the hair was dyed in a mahogany red shade quite resistant to light, shampooing and adverse weather conditions.

EXAMPLE 4

The following dyeing composition was prepared:
Apigenidin chloride prepared
in Example 1 1.00 g
Hydroxyethylcellulose 2.66 g
Ethyl alcohol 16.00 g
Aqueous solution of NaOH qs pH 9.5
Demineralized water qs 100 g The above composition was applied to locks of natural grey hair and also to locks of permanently-waved grey hair, which was 90% white, at the rate of 2 grams of composition per gram of hair. It was allowed to act for 30 minutes at 45° C. After rinsing with running water and drying, the hair was dyed in a mahogany red shade quite resistant to shampooing, perspiration and light.

EXAMPLE 5

The following dyeing composition was prepared:

Apigenidin chloride prepared
in Example 1 1.00 g
Hydroxyethylcellulose 2.66 g
Ethyl alcohol 16.00 g
Aqueous solution of HCl qs pH 5.5
Demineralized water qs 100 g The above composition was applied to locks of natural grey hair and also to locks of permanently-waved grey hair, which was 90% white, at the rate of 2 grams of composition per gram of hair. It was allowed to act for 30 minutes at 45° C. After rinsing with running water and drying, the hair was dyed in a mahogany red shade quite resistant to shampooing, perspiration and light.

What is claimed is:

1. A composition for dyeing keratinous fibers, comprising a medium appropriate for dyeing and at least one flavylium compound containing a flavylium ring (F):

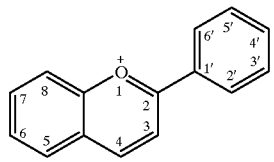

(F)

wherein said flavylium ring is non-substituted at position 3, is substituted at any other position by at least one radical chosen from hydroxyl and alkoxy radicals, and is further optionally substituted at position 4' by a hydroxyalkyl radical, and further wherein said at least one flavylium compound is in pure form or in the form off plant extract containing said at least one flavylium compound;

wherein the at least one flavylium compound is present in the composition in an amount effective for dyeing keratinous fibers ranging from 0.05 to 20% relative to the total weight of the composition.

2. A composition according to claim 1, wherein said keratinous fibers are human keratinous fibers.

3. A composition according to claim 2, wherein said human keratinous fibers are human hair.

4. A composition according to claim 1, wherein said at least one flavylium compound is substituted at position 4' by a hydroxyl, alkoxy or hydroxyalkyl radical.

5. A composition according to claim 4, wherein said at least one flavylium compound is a compound of the following formula (I):

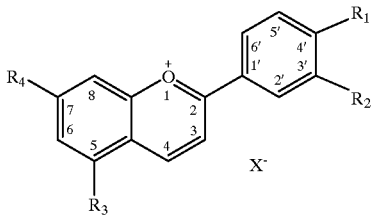

(I)

in which:
R₁ is chosen from a hydroxyl radical or a saturated or unsaturated, linear or branched $C_1$–$C_8$ alkoxy radical,
R₂, R₃ and R₄, which are identical or different, are chosen from hydrogen, a hydroxyl radical or a saturated or unsaturated, linear or branched $C_1$–$C_8$ alkoxy radical, and
X⁻ is an anion,
wherein at least one of R₁ to R4, is a hydroxyl radical.

6. A composition according to claim 5, wherein said X⁻ is chosen from a halogen and a radical:

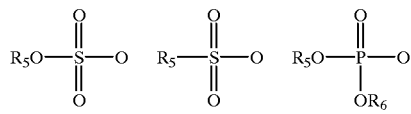

in which R₅ and R₆ are chosen from saturated or unsaturated, linear or branched $C_1$–$C_8$ alkyl radicals.

7. A composition according to claim 5, wherein, in formula (I), R₁ is chosen from OH or OCH₃.

8. A composition according to claim 5, wherein said compound of formula (I) is chosen from a group comprising the chlorides of:
4',5,7-trihydroxyflavylium,
3',4',7-trihydroxyflavylium,
4'-hydroxyflavylium,
4',7-dihydroxyflavylium,
3',4-dihydroxyflavylium, and
3',4dihydroxy-7-methoxyflavylium.

9. A composition according to claim 8, wherein said compound of formula (I) is 4',5,7-trihydroxyflavylium chloride in pure form.

10. A composition according to claim 8, wherein said compound of formula (I) is 4',5,7-trihydroxyflavylium chloride in the form of a plant extract.

11. A composition according to claim 10, wherein said plant extract is an extract of *Sorghum caudatum*.

12. A composition according to claim 11, wherein said 4',5,7-trihydroxyflavylium chloride is present in said extract in a titre greater than 70%.

13. A composition according to claim 1, wherein said composition has a pH ranging from 2 to 10.

14. A composition according to claim 1, wherein said composition has a pH ranging from 5 to 10.

15. A composition according to claim 1, wherein said at least one flavylium compound is present in a concentration ranging from 0.1 to 10% relative to the total weight of the composition.

16. A composition according to claim 1, wherein said composition further comprises a medium suitable for dyeing, said medium comprising water or organic solvents or a mixture thereof.

17. A composition according to claim 16, wherein said organic solvents are chosen from alcohols, glycols and glycol ethers.

18. A composition according to claim 1, further comprising at least one additional direct dye, wherein said at least one additional direct dye is chosen from natural and synthetic direct dyes and is different from said at least one flavylium compound.

19. A composition according to claim 18, wherein said natural dyes are chosen from 2,3-indolinedione, hydroxyanthraquinones, and benzoquinones.

20. A composition according to claim 18, wherein said synthetic dyes are chosen from nitrobenzene, nitropyridine, anthraquinone, monoazo, diazo, triarylmethane, azine, acridine, xanthene and metalliferous dyes.

21. A composition according to claim 1, further comprising at least one additional ingredient chosen from fatty amides, surfactants; thickening agents, antioxidants, perfumes, sequestering agents, dispersing agents, hair conditioning agents, preservatives and opacifying agents.

22. A method of dyeing human keratinous fibers, by direct dyeing, wherein said method comprises:
applying to dry or wet keratinous fibers a dyeing composition comprising as a coloring agent at least one flavylium compound containing a flavylium ring (F):

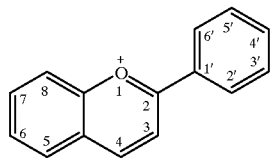

(F)

wherein said flavylium ring is non-substituted at position 3, is substituted at any other position by at least one radical chosen from hydroxyl and alkoxy radicals, and is further optionally substituted at position 4' by a hydroxyalkyl radical, and further wherein said at least one flavylium compound is in pure form or in the form of plant extracts containing them,
wherein the at least one flavylium compound is present in the dyeing composition in an amount effective for dyeing the fibers.
optionally allowing said composition to act on the fibers for an exposure time period ranging from 3 to 60 minutes, at a temperature ranging from 20° C. to 50° C., optionally rinsing said fibers, and then drying said fibers.

23. A method according to claim 22, wherein said human keratinous fibers are hair.

24. A method according to claim 22, wherein said at least one flavylium compound is substituted at position 4' by a hydroxyl, alkoxy or hydroxyalkyl radical.

25. A method according to claim 22, wherein said at least one flavylium compound is a compound of the following formula (I):

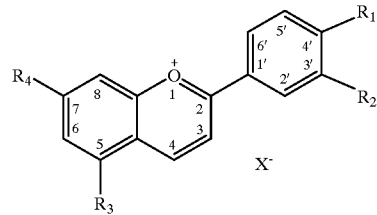

(I)

in which:
R₁ is chosen from a hydroxyl radical or a saturated or unsaturated, linear or branched $C_1$–$C_8$ alkoxy radical,
R₂, R₃ and R₄, which are identical or different, are chosen from hydrogen, a hydroxyl radical or a saturated or unsaturated, linear or branched $C_1$–$C_8$ alkoxy radical, and
X⁻ is an anion,
wherein at least one of R₁ to R₄ is hyroxyl radical.

26. A method according to claim 25, wherein said X⁻ is chosen from a halogen and a radical:

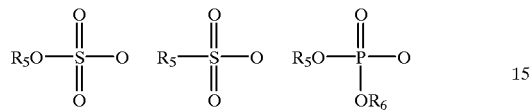

in which $R^5$ and $R_6$ are chosen from saturated or unsaturated, linear or branched $C_1$–$C_8$ alkyl radicals.

27. A method according to claim 25, wherein, in formula (I), R₁ is chosen from OH or OCH₃.

28. A method according to claim 25, wherein said compound of formula (I) is chosen from a group comprising the chlorides of:
4',5,7-trihydroxyflavylium,
3',4',7-trihydroxyflavylium,
4'-hydroxyflavylium,
4',7-dihydroxyflavylium,
3',4-dihydroxyflavylium, and
3',4'-dihydroxy-7-methoxyflavylium.

29. A method according to claim 28, wherein said compound of formula (I) is 4',5,7-trihydroxyflavylium chloride in pure form.

30. A method according to claim 28, wherein said compound of formula (I) is 4',5,7-trihydroxyflavylium chloride in the form of a plant extract.

31. A method according to claim 30, wherein said plant extract is an extract of *Sorghum caudatum*.

32. A method according to claim 31, wherein said 4',5,7-trihydroxyflavylium chloride is present in said extract in a titre greater than 70%.

33. A method for the preparation of a composition for dyeing keratinous fibers, said method comprising the step of including in said composition as a coloring agent at least one flavylium compound containing a flavylium ring (F):

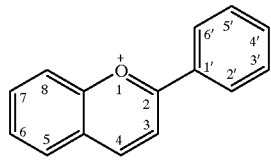

wherein said flavylium ring is non-substituted in position 3, is substituted at any other position by at least one radical chosen from hydroxyl, and alkoxy radicals, and is further optionally substituted at position 4' by a hydroxyalkyl radical, and further wherein said at least one flavylium compound is in pure form or in the form of plant extracts containing said flavylium compound, and a medium appropriate for dyeing, wherein said at least one flavylium compound is present in an amount effective for dyeing said keratinous fibers ranging from 0.05 to 20% relative to the total weight of the composition.

\* \* \* \* \*

UNITED STATES PATENT AND TRADEMARK OFFICE
CERTIFICATE OF CORRECTION

PATENT NO. : 6,241,785 B1
DATED : June 5, 2001
INVENTOR(S) : Patrick Darmenton et al.

Page 1 of 1

It is certified that error appears in the above-identified patent and that said Letters Patent is hereby corrected as shown below:

Column 10, claim 1,
Line 51, "off" should read -- of --.

Column 11, claim 9,
Line 44, "4'5,7" should be unsuperscripted.

Column 11, claim 13,
Line 55, "10" should read -- 11 --.

Column 13, claim 25,
Line 9, insert "a" before hydroxyl.

Signed and Sealed this

Twelfth Day of March, 2002

*Attest:*

*Attesting Officer*

JAMES E. ROGAN
*Director of the United States Patent and Trademark Office*